US012733887B2

(12) United States Patent
Lewis et al.

(10) Patent No.: US 12,733,887 B2
(45) Date of Patent: Sep. 15, 2026

(54) SYSTEMS AND METHODS FOR DETERMINING A TIMING BOLUS DELAY

(71) Applicant: GE Precision Healthcare LLC, Waukesha, WI (US)

(72) Inventors: Chelsey Lewis, Waukesha, WI (US); Cecilia Cortez, Sussex, WI (US); Christine Hammond, Oconomowoc, WI (US); Pamela McNicol, Waukesha, WI (US); Bhabani Pattanayak, Waukesha, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 128 days.

(21) Appl. No.: 18/590,587

(22) Filed: Feb. 28, 2024

(65) Prior Publication Data

US 2025/0268541 A1 Aug. 28, 2025

(51) Int. Cl.

| | |
|---|---|
| ***A61B 6/03*** | (2006.01) |
| ***A61B 6/00*** | (2006.01) |
| ***A61B 6/46*** | (2024.01) |
| ***A61B 6/50*** | (2024.01) |

(52) U.S. Cl.

CPC ................ *A61B 6/03* (2013.01); *A61B 6/465* (2013.01); *A61B 6/481* (2013.01); *A61B 6/50* (2013.01)

(58) Field of Classification Search

None

See application file for complete search history.

(56) References Cited

U.S. PATENT DOCUMENTS

| | | | | |
|---|---|---|---|---|
| 8,755,865 | B2 | 6/2014 | Gonzalez Molezzi | |
| 9,456,798 | B2 | 10/2016 | Xue | |
| 2002/0107438 | A1* | 8/2002 | Liu | G01R 33/5601 600/410 |
| 2008/0253634 | A1 | 10/2008 | Hay | |
| 2010/0113887 | A1 | 5/2010 | Kalafut | |
| 2015/0324979 | A1 | 11/2015 | Xue | |
| 2022/0061793 | A1* | 3/2022 | Vaz | G06N 3/09 |

FOREIGN PATENT DOCUMENTS

| | | | |
|---|---|---|---|
| JP | 2003102724 | A | 4/2003 |
| JP | 2016032764 | A | 3/2016 |
| WO | 2023187370 | W | 10/2023 |

OTHER PUBLICATIONS

EP application 25157053.7 filed Feb. 11, 2025—extended Search Report issued Jul. 16, 2025, 8 pages.
JP application 2025-016353 filed Feb. 3, 2025—Office Action issued Nov. 5, 2025; Machine Translation; 5 pages.
JP2003102724 Machine Translation, 23 pages.

* cited by examiner

*Primary Examiner* — Hoon K Song

(57) ABSTRACT

Embodiments of the present disclosure relate to a method for determining a timing bolus delay. The method can include administering a test bolus to a subject; acquiring, via a computed tomography (CT) imaging system, a plurality of images of the subject; determining a contrast value for each of the plurality of images; generating a contrast curve based on the determined contrast values; determining a peak contrast value on the contrast curve; determining a prep delay based on the peak contrast value; and administering a contrast-enhanced CT scan of the subject based on the determined prep delay.

20 Claims, 6 Drawing Sheets

SYSTEMS AND METHODS FOR DETERMINING A TIMING BOLUS DELAY

BACKGROUND OF THE DISCLOSURE

A common type of diagnostic examination is a computed tomography (CT) imaging exam which is used to diagnose disease or injury by creating images of various parts of the human body, including bones, blood vessels, and soft tissue. Occasionally, a patient may need a CT scan with contrast, where the patient receives an injection of a contrast agent prior to the scan. The contrast agent attenuates X-rays and helps identify and highlight certain areas of the body on the CT images that allow for more accurate and detailed diagnosis to be made by a relevant medical professional. For example, a contrast agent may enhance the visibility of tumors, inflammation, blood vessels, blood supplies of certain organs, etc.

SUMMARY OF THE DISCLOSURE

According to one aspect of the present disclosure, a method for determining a timing bolus delay can include administering a test bolus to a subject; acquiring, via a computed tomography (CT) imaging system, a plurality of images of the subject; determining a contrast value for each of the plurality of images; generating a contrast curve based on the determined contrast values; determining a peak contrast value on the contrast curve; determining a prep delay based on the peak contrast value; and administering a contrast-enhanced CT scan of the subject based on the determined prep delay.

In some embodiments, administering the test bolus to the subject can include injecting a contrast agent into the subject. In some embodiments, determining the prep delay based on the peak contrast value can include an automated determination of a total elapsed time from the administering of the test bolus to the peak contrast value. In some embodiments, the automated determination of the total elapsed time can include analyzing at least one of a relative Hounsfield unit (HU) change, an absolute HU change, or a predefined percent of the peak contrast value being reached.

In some embodiments, the method can include receiving a selection from a user via a user interface; and at least one of analyzing the at least one of the relative Hounsfield unit (HU) change, the absolute HU change, or the predefined percent of the peak contrast value being reached based on the received selection. In some embodiments, the method can include receiving a definition of a region of interest from a user via a user interface; and manipulating the contrast curve based on the definition of the region of interest. In some embodiments, the method can include augmenting the total elapsed time with a predetermined modifier. In some embodiments, the predetermined modifier can be configured by a user via a user interface. In some embodiments, acquiring the plurality of images of the subject can include acquiring one image every second for ten seconds.

According to another aspect of the present disclosure, a method for determining a timing bolus delay can include administering a test bolus to a subject; acquiring, via a computed tomography (CT) imaging system, a plurality of images of the subject; determining a contrast value for each of the plurality of images; generating a contrast curve based on the determined contrast values; identifying a plateau on the contrast curve; determining a prep delay based on the identified plateau; and administering a contrast-enhanced CT scan of the subject based on the identified plateau.

In some embodiments, administering the test bolus to the subject can include injecting a contrast agent into the subject. In some embodiments, determining the prep delay based on the identified plateau can include an automated determination of a total elapsed time from the administering of the test bolus to the identified plateau. In some embodiments, the automated determination of the total elapsed time can include analyzing at least one of a relative Hounsfield unit (HU) change, an absolute HU change, or a predefined percent of a peak contrast value being reached.

In some embodiments, the method can include receiving a selection from a user via a user interface; and at least one of analyzing the at least one of the relative Hounsfield unit (HU) change, the absolute HU change, or the predefined percent of the peak contrast value being reached based on the received selection. In some embodiments, the method can include receiving a definition of a region of interest from a user via a user interface; and manipulating the contrast curve based on the definition of the region of interest.

In some embodiments, the method can include augmenting the total elapsed time with a predetermined modifier. In some embodiments, the predetermined modifier can be configured by a user via a user interface. In some embodiments, the plateau can occur in a designated location after a peak contrast value. In some embodiments, acquiring the plurality of images of the subject can include acquiring one image every second for ten seconds.

According to another aspect of the present disclosure, a system for determining a timing bolus delay can include a computed tomography (CT) imaging system configured to acquire a plurality of images of a subject after a test bolus has been administered to the subject; and a computing device that can include a processor and a non-transitory computer-readable storage device storing computer-executable instructions. The instructions can be operable to cause the processor to perform operations comprising: receiving the plurality of images of the subject from the CT imaging system; determining a contrast value for each of the plurality of images; generating a contrast curve based on the determined contrast values; determining a peak contrast value on the contrast curve; and determining a prep delay based on the peak contrast value.

BRIEF DESCRIPTION OF THE FIGURES

Various objectives, features, and advantages of the disclosed subject matter can be more fully appreciated with reference to the following detailed description of the disclosed subject matter when considered in connection with the following drawings, in which like reference numerals identify like elements.

Figure 1:
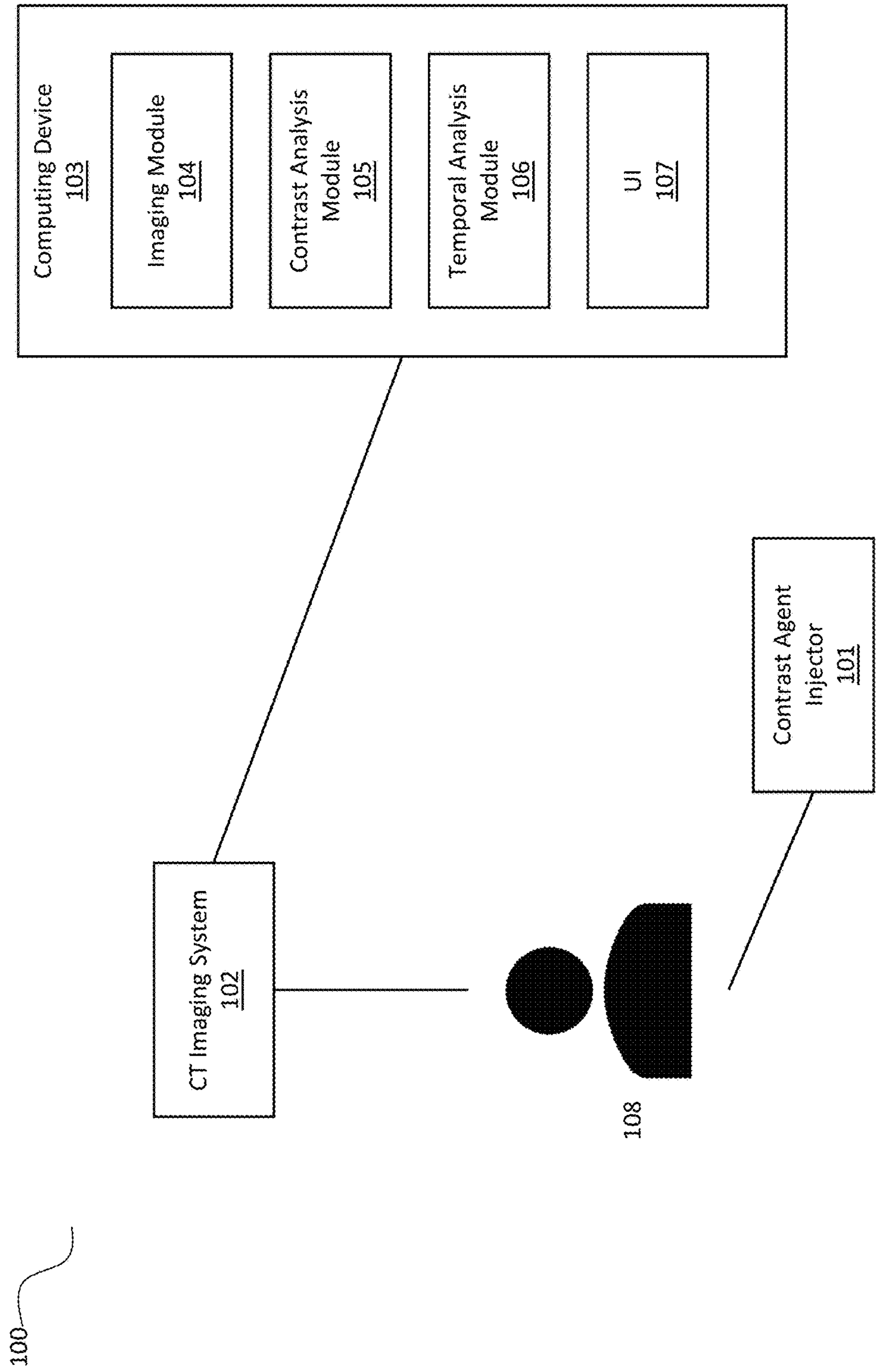
FIG. 1 is a block diagram of an example system for automatically determining a timing bolus delay according to some embodiments of the present disclosure.

The drawings are not necessarily to scale, or inclusive of all elements of a system, emphasis instead generally being placed upon illustrating the concepts, structures, and techniques sought to be protected herein.

DESCRIPTION

The following detailed description is merely exemplary in nature and is not intended to limit the claimed invention or the applications of its use.

Timing is an important aspect of contrast-enhanced CT imaging techniques. In particular, it is highly desirable for the data acquisition (i.e., the CT imaging system) to be synchronized with the administration of a contrast agent. In other words, it is highly desirable for the CT imaging system to perform the imaging while the contrast agent is passing through the region of interest in the patient's body. This can maximize the quality of the images and enhance particular structures within the images that are obtained by the imaging system. To synchronize such timing and achieve the highest accuracy in such imaging, a common technique is to employ a test bolus to identify the "delay" of the contrast moving from the injection site to the region of interest. A test bolus is a small "test" quantity of the contrast agent that is administered to the patient (i.e., via injection). The CT imaging system can then monitor the uptake of the contrast in the imaging area, taking a certain number of images at a predefined frequency (e.g., one image per second for ten seconds). The contrast of each image is then plotted as a function of time, for example as a scatter plot. A user must then evaluate the graph manually, usually counting the points and adding some initial number manually to estimate the given delay. The estimated delay is then used when the real contrast agent is administered to ensure the timing is optimal. However, such manual calculations are unreliable, tedious, slow, and generally undesirable.

Accordingly, embodiments of the present disclosure are directed to systems and methods for automatically determining a timing bolus delay. The disclosed techniques involve administering a test bolus to a subject and acquiring a plurality of CT images (which generally includes a series of X-ray images) of the region of interest on the subject over a period of time after the test bolus has been administered. The images can then be sent to a computing device for analysis, where contrast values are determined for each image. The contrast values are then plotted, and the computing device automatically identifies the image with a peak contrast value. Then, the computing device calculates the time that elapsed from injection of the test bolus to the peak contrast value. This elapsed time (i.e., the "prep delay") can then be used to administer the full contrast-enhanced CT scan. In addition, various plots, such as the contrast curve, can be displayed in a user interface to the technician or other person administering the CT scan. In addition, the disclosed system allows for significant customization on behalf of the technician. For example, rather than automatically using the determined prep delay, the technician can, via the user interface, manually edit the delay. In other embodiments, the user can customize what values are calculated and displayed via the user interface. For example, rather than peak contrast, the system can calculate and display the peak plus some buffer, time at a predefined percentage of the peak, time at Hounsfield units (HU) enhance threshold (relative or absolute), and others.

FIG. 1 is a block diagram of an example system 100 for automatically determining a timing bolus delay according to some embodiments of the present disclosure. The system 100 can be used for administering contrast-enhanced CT scans of a subject 108. The system 100 can include a contrast agent injector 101, which is configured to inject or otherwise administer contrast agents to the subject 108. The contrast agent injector 101 can inject both a test bolus and the full contrast agent to the subject 108. In addition, the system 100 can include a CT imaging system 102 that is configured to perform CT imaging techniques to acquire various images (e.g., X-ray images) of the patient. For example, the CT imaging system 102 can include a subject table and cradle for receiving the subject for insertion into a gantry that includes an X-ray source and X-ray detector array that rotate around the subject during a CT imaging technique when acquiring images of the subject, and a control device to implement various methods described herein. In some embodiments, the acquired images are non-diagnostic images, meaning the images are not used for diagnosing any pathologies. Instead, the images are used for bolus timing only.

In addition, the system 100 can include a computing device 103 that is communicably coupled to the CT imaging system 102 to receive the images acquired therefrom. The computing device 103 can include an imaging module 104, a contrast analysis module 105, a temporal analysis module 106, and a user interface (UI) 107. In some embodiments, the imaging module 104 is configured to receive images acquired by the CT imaging system 102 and, for example, cause them to be displayed via the UI 107 of the computing device 103. In some embodiments, the contrast analysis module 105 is configured to analyze the images received from the CT imaging system 102. For example, the contrast analysis module 105 can measure/detect/calculate/determine levels of contrast (i.e., "contrast values") of each of the acquired images. In addition, the contrast analysis module 105 can generate contrast curves, which can be plots of the contrast values of the images over time and identify peak contrast values from the series of images. In some embodiments, the temporal analysis module 106 is configured to determine an elapsed time (i.e., "prep delay") from a time of injection of a test bolus to the peak contrast value. The temporal analysis module 106 can then, in some embodiments, automatically program the CT imaging system 102 to perform a subsequent CT imaging protocol using the determined prep delay. In addition, the UI 107 allows a technician or other user (e.g., a radiologist) to interact with the system and to customize various details of the contrast analysis and prep delay calculations.

In some embodiments, the computing device 103 can include one or more computing devices capable of receiving user input via the UI 107, transmitting and/or receiving data via a network, and or communicating with the CT imaging system 102. In some embodiments, a computing device 103 can be a conventional computer system, such as a desktop or laptop computer or a standalone computer, server, or other computer system. Alternatively, a computing device 103 can include a device having computer functionality, such as a personal digital assistant (PDA), a mobile telephone, a smartphone, tablet, or other suitable device. In some embodiments, a computing device 103 can be the same as or similar to the computing device 600 described below with respect to FIG. 6.

Figure 2:
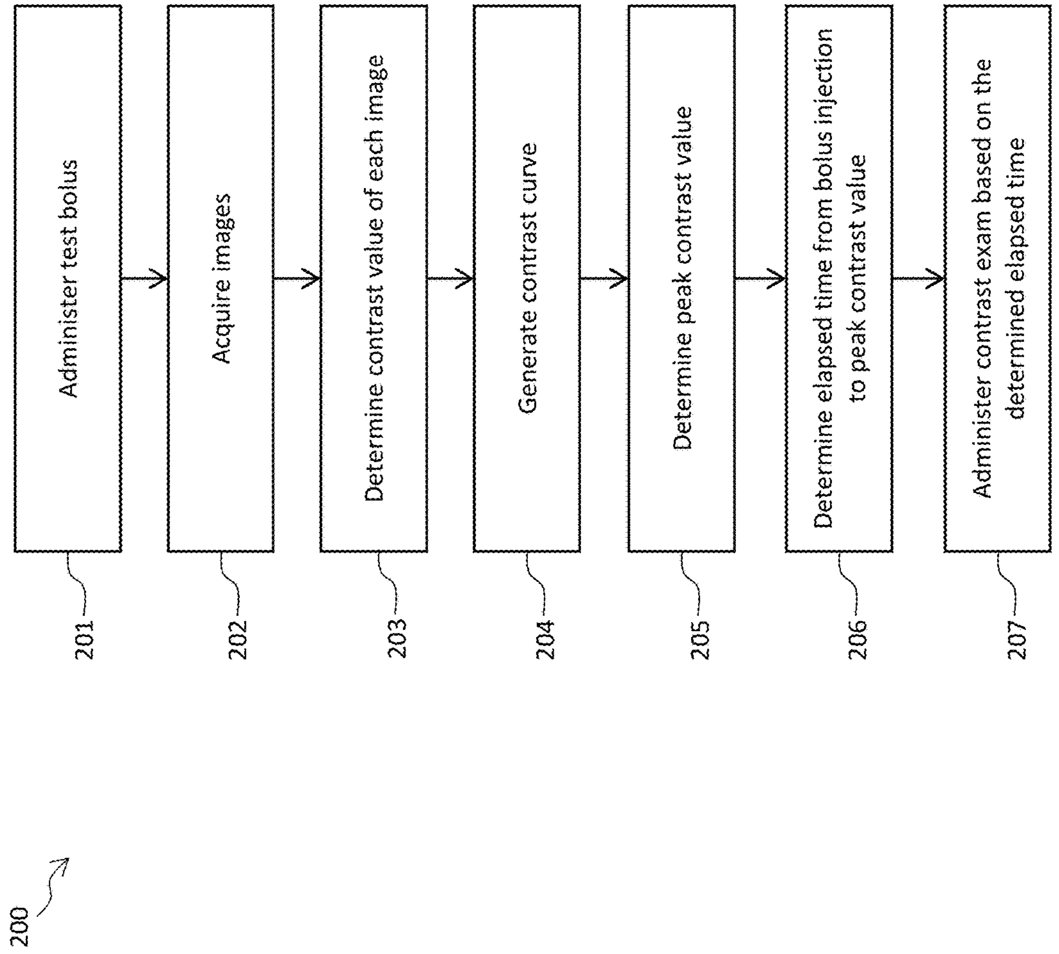
FIG. 2 is a flowchart of an example process for automatically determining a timing bolus delay according to example embodiments of the present disclosure.

FIG. 2 is a flowchart of an example process 200 for automatically determining a timing bolus delay according to example embodiments of the present disclosure. In some embodiments, the process 200 can be performed by the computing device 103 in conjunction with a test bolus and full contrast-enhanced CT imaging scan being administered to the subject 108. At block 201, the contrast agent injector 101 administers a test bolus to the subject 108. In some embodiments, the administering can be performed by injecting a contrast agent into an arm of the subject 108.

At block 202, the CT imaging system 102 acquires a plurality of images of the subject 108. For example, the images can be obtained via standard CT scanning techniques that are generally used. In some embodiments, the CT imaging system 102 can obtained a predefined number of images at a predefined frequency, such as one image every second for a total of ten seconds. The acquired images can then be sent to the imaging module 104 of the computing device 103 for analysis. At block 203, the contrast analysis module 105 determines a contrast value of each image. In some embodiments, the contrast value can be express in HU, which is a standard relative quantitative measurement of radio density.

At block 204, the contrast analysis module 105 generates a contrast curve. In some embodiments, this can include plotting the contrast value determined for each image as a function of time. In some embodiments, the contrast curve is displayed to the technician on the computing device 103 via the UI 107. From here, the technician can perform various customizations. For example, the technician can manipulate the contrast curve through a region of interest being placed on the anatomy of the subject. At block 205, the temporal analysis module 106 determines the peak contrast value of the contrast curve. For example, the temporal analysis module 106 can identify the point (which corresponds to one of the acquired images) on the contrast curve that has a maximum Hounsfield unit (HU) value. At block 206, the temporal analysis module 106 can then determine the elapsed time from the injection of the test bolus to the point in time at which the peak contrast value was obtained. This is set as the prep delay. In addition, the peak contrast value in HU and the total elapsed time can be displayed to the technician via the UI 107. In some embodiments, the total elapsed time can be determined via a relative HU change, an absolute HU change, or a predefined percentage of the peak contrast being achieved. In some embodiments, the total elapsed time can be augmented by a predetermined modifier of time (e.g., +/−x time as defined by the technician). At block 207, a full contrast CT scan of the subject is administered based on the determined prep delay.

Figure 3:
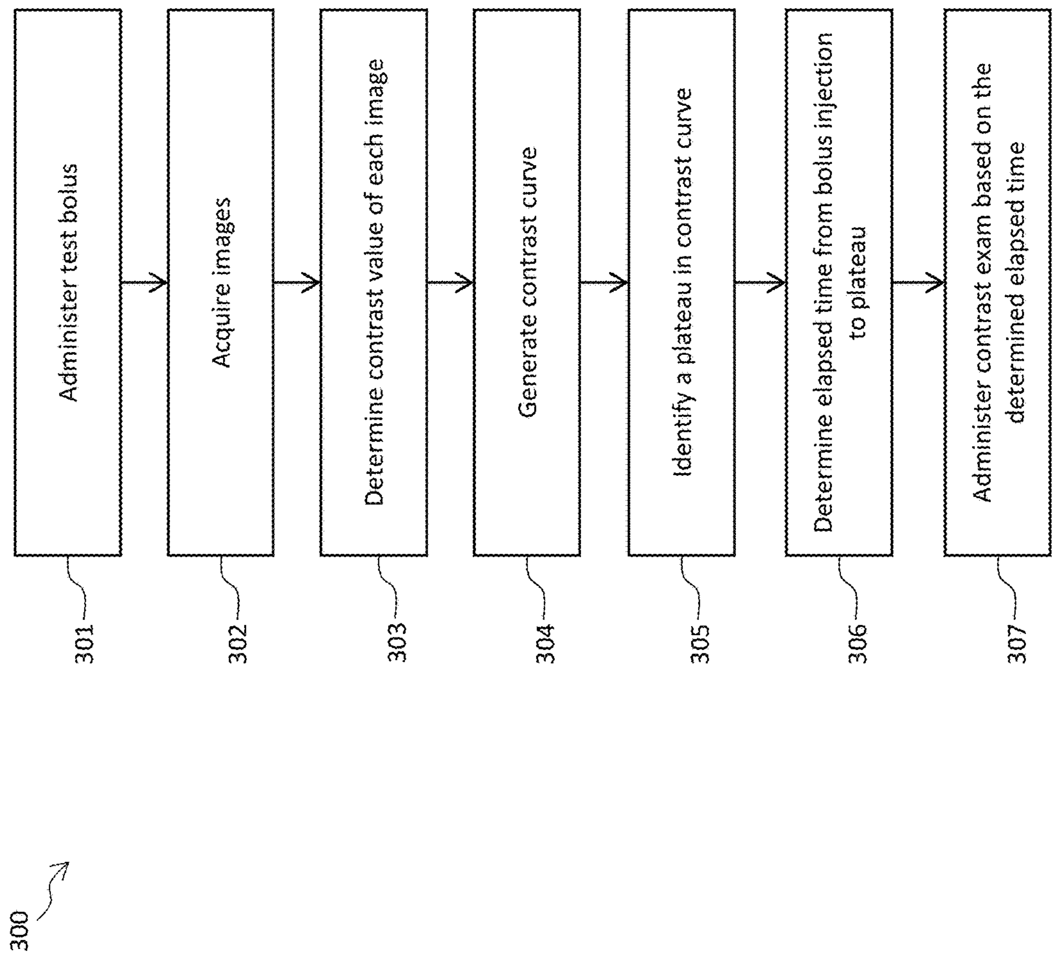
FIG. 3 is another flowchart of an example process for automatically determining a timing bolus delay according to example embodiments of the present disclosure.

FIG. 3 is another flowchart of an example process 300 for automatically determining a timing bolus delay according to example embodiments of the present disclosure. In some embodiments, the process 300 can be performed by the computing device 103 in conjunction with a test bolus and full contrast-enhanced CT scan being administered to the subject 108. In addition, the process 300 can be performed for automated intergroup delay calculations for a contrast exam with contrast washout has occurred. At block 301, the contrast agent injector 101 administers a test bolus to the subject 108. In some embodiments, the administering can be performed by injecting the agent into an arm of the subject 108.

At block 302, the CT imaging system 102 acquires a plurality of images of the subject 108. For example, the images can be obtained via standard CT scanning techniques that are generally used. In some embodiments, the CT imaging system 102 can acquire a predefined number of images at a predefined frequency, such as one image every second for a total of ten seconds. The acquired images can then be sent to the imaging module 104 of the computing device 103 for analysis. At block 303, the contrast analysis module 105 determines a contrast value of each image. In some embodiments, the contrast value can be express in HU, which is a standard relative quantitative measurement of radio density.

At block 304, the contrast analysis module 105 generates a contrast curve. In some embodiments, this can include plotting the contrast value determined for each image as a function of time. In some embodiments, the contrast curve is displayed to the technician on the computing device 103 via the UI 107. From here, the technician can perform various customizations. For example, the technician can manipulate the contrast curve through a region of interest being placed on the anatomy of the subject. At block 305, the temporal analysis module 106 identifies a plateau (i.e., washout) in the contrast curve. In some embodiments, the plateau can be identified in a designated location after the peak contrast value. At block 306, the temporal analysis module 106 can then determine the elapsed time from the injection of the test bolus to the point in time at which the peak contrast value was obtained. This is set as the prep delay. In addition, the peak contrast value in HU and the total elapsed time can be displayed to the technician via the UI 107. In some embodiments, the total elapsed time can be determined via a relative HU change, an absolute HU change, or a predefined percentage of the peak contrast being achieved. In some embodiments, the total elapsed time can be augmented by a predetermined modifier of time (e.g., +/−x time as defined by the technician). At block 307, a full contrast CT scan of the subject is administered based on the determined prep delay. For example, the determined time can be set as the group delay of a subsequent contrast acquisition group for washout.

Figure 4A:
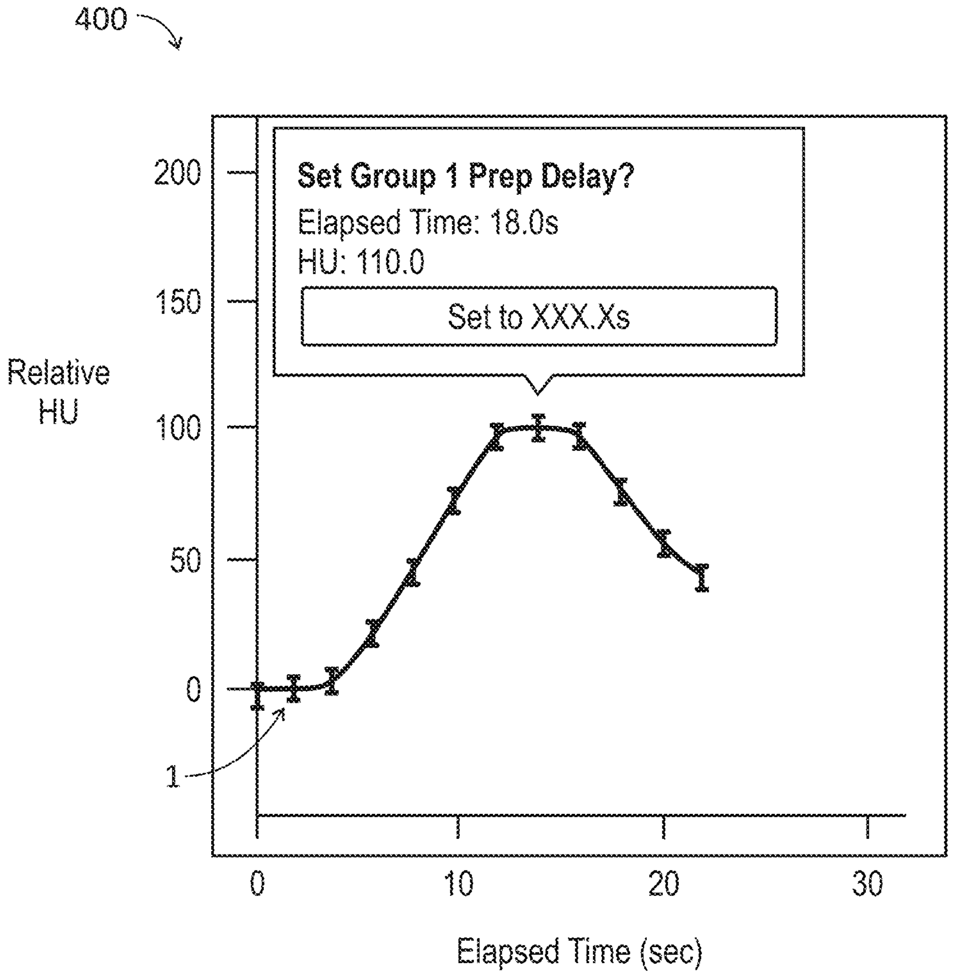
FIGS. 4A-4B are example user interfaces that can be displayed within the system of FIG. 1 according to an embodiment of the present disclosure.
Figure 4B:
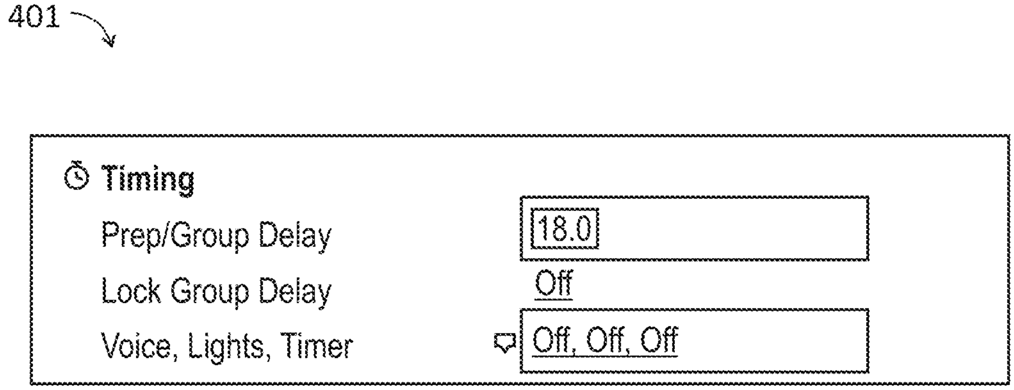

FIGS. 4A-4B are example user interfaces that can be displayed within the system of FIG. 1 according to an embodiment of the present disclosure. FIG. 4A shows an example contrast curve 400 that can displayed via UI 107 on the computing device 103, where the x-axis represents time and the y-axis represents HU. The ticks are plotted as points of HU values from each of the images acquired by the CT imaging system 102, and the line is automatically drawn based on the plotted points. The contrast curve 400 also includes an automated popup that displays the automatically calculated elapsed time (18.0 s) and the peak contrast value (110.0 HU). In some embodiments, the popup can include a button, selectable by the technician, that applies the elapsed time as the prep delay for a subsequent contrast-enhanced CT imaging process. FIG. 4B shows an interface 401 that can also be displayed via UI 107 on the computing device 103. In interface 401, the prep delay is automatically set to the elapsed time (18.0 s) from the contrast curve, but the value is editable by the technician.

Figure 5:
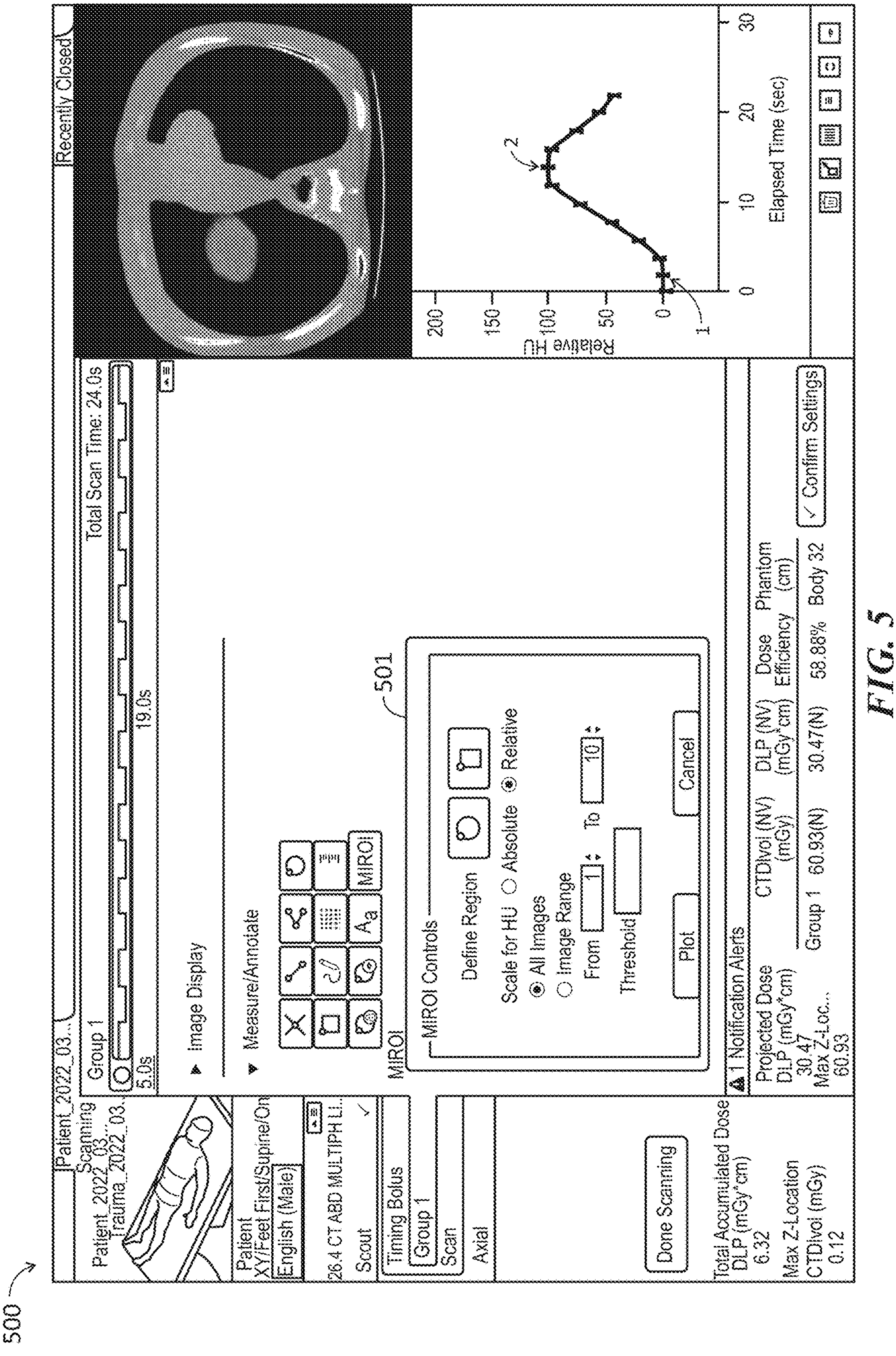
FIG. 5 is another example user interface that can be displayed within the system of FIG. 1 according to an embodiment of the present disclosure.

FIG. 5 is another example user interface 500 that can be displayed within the system of FIG. 1 according to an embodiment of the present disclosure. The interface 500 can be displayed via the UI 107 on the computing device 103. The interface 500 displays the CT imaging of the subject 108, as well as the contrast curve that is generated after the administration of a test bolus. In addition, the interface 500 can include a control panel 501 that allows a technician to perform various controls of the CT imaging system 102, such as the type of HU (absolute vs. relative), defining a region of interest, or setting an HU threshold.

Figure 6:
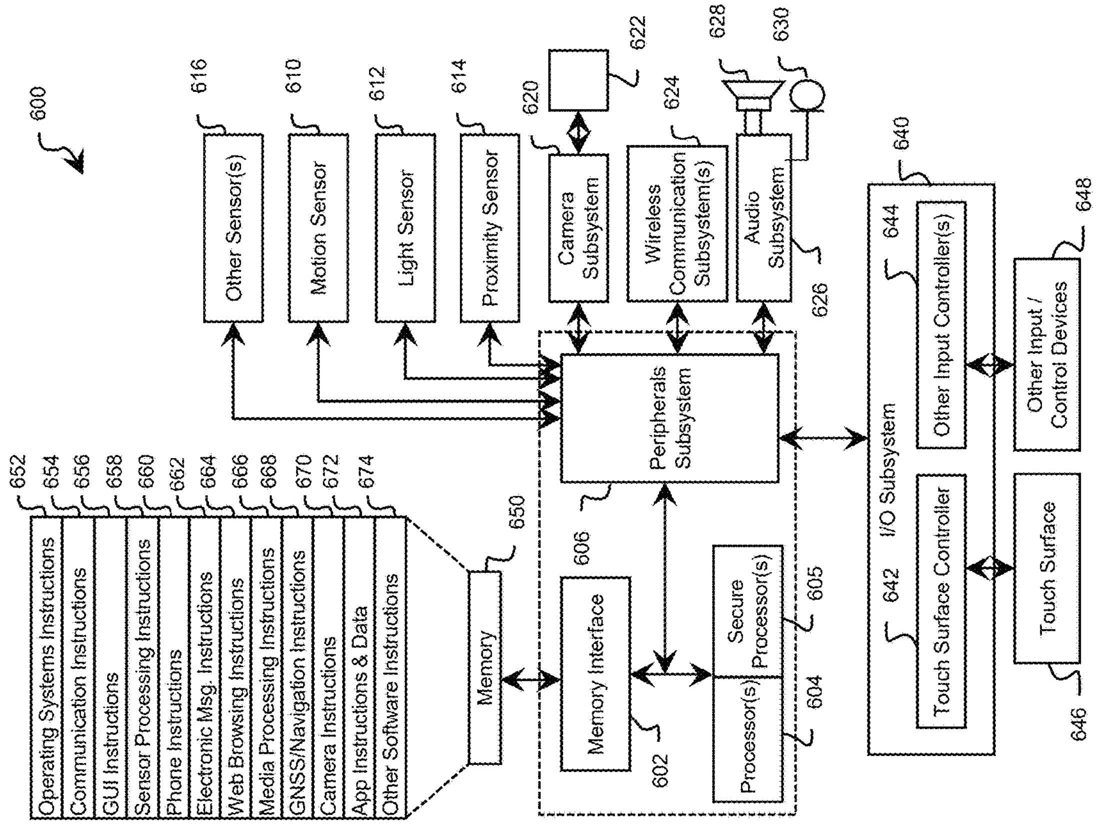
FIG. 6 is an example computing device that can be used within the system of FIG. 1 according to an embodiment of the present disclosure.

FIG. 6 is an example computing device that can be used within the system of FIG. 1 according to an embodiment of the present disclosure. In some embodiments, device 600 can be computing device 103. The illustrative user device 600 can include a memory interface 602, one or more data processors, image processors, central processing units 604, and or secure processing units 605, and peripherals subsystem 606. Memory interface 602, one or more central processing units 604 and or secure processing units 605, and or peripherals subsystem 606 can be separate components or can be integrated in one or more integrated circuits. The various components in user device 600 can be coupled by one or more communication buses or signal lines.

Sensors, devices, and subsystems can be coupled to peripherals subsystem 606 to facilitate multiple functionalities. For example, motion sensor 610, light sensor 612, and proximity sensor 614 can be coupled to peripherals subsystem 606 to facilitate orientation, lighting, and proximity functions. Other sensors 616 can also be connected to peripherals subsystem 606, such as a global navigation satellite system (GNSS) (e.g., GPS receiver), a temperature sensor, a biometric sensor, magnetometer, or other sensing device, to facilitate related functionalities.

Camera subsystem 620 and optical sensor 622, e.g., a charged coupled device (CCD) or a complementary metal-oxide semiconductor (CMOS) optical sensor, can be utilized to facilitate camera functions, such as recording photographs and video clips. Camera subsystem 620 and optical sensor 622 can be used to collect images of a user to be used during authentication of a user, e.g., by performing facial recognition analysis.

Communication functions can be facilitated through one or more wired and or wireless communication subsystems 624, which can include radio frequency receivers and transmitters and or optical (e.g., infrared) receivers and transmitters. For example, the Bluetooth (e.g., Bluetooth low energy (BTLE)) and or WiFi communications described herein can be handled by wireless communication subsystems 624. The specific design and implementation of communication subsystems 624 can depend on the communication network(s) over which the user device 600 is intended to operate. For example, user device 600 can include communication subsystems 624 designed to operate over a GSM network, a GPRS network, an EDGE network, a WiFi or WiMax network, and a Bluetooth™ network. For example, wireless communication subsystems 624 can include hosting protocols such that device 600 can be configured as a base station for other wireless devices and or to provide a WiFi service.

Audio subsystem 626 can be coupled to speaker 628 and microphone 630 to facilitate voice-enabled functions, such as speaker recognition, voice replication, digital recording, and telephony functions. Audio subsystem 626 can be configured to facilitate processing voice commands, voice-printing, and voice authentication, for example.

I/O subsystem 640 can include a touch-surface controller 642 and or other input controller(s) 644. Touch-surface controller 642 can be coupled to a touch-surface 646. Touch-surface 646 and touch-surface controller 642 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with touch-surface 646.

The other input controller(s) 644 can be coupled to other input/control devices 648, such as one or more buttons, rocker switches, thumb-wheel, infrared port, USB port, and or a pointer device such as a stylus. The one or more buttons (not shown) can include an up/down button for volume control of speaker 628 and or microphone 630.

In some implementations, a pressing of the button for a first duration can disengage a lock of touch-surface 646; and a pressing of the button for a second duration that is longer than the first duration can turn power to user device 600 on or off. Pressing the button for a third duration can activate a voice control, or voice command, module that enables the user to speak commands into microphone 630 to cause the device to execute the spoken command. The user can customize a functionality of one or more of the buttons. Touch-surface 646 can, for example, also be used to implement virtual or soft buttons and or a keyboard.

In some implementations, user device 600 can present recorded audio and or video files, such as MP3, AAC, and MPEG files. In some implementations, user device 600 can include the functionality of an MP3 player, such as an iPod™. User device 600 can, therefore, include a 36-pin connector and or 8-pin connector that is compatible with the iPod. Other input/output and control devices can also be used.

Memory interface 602 can be coupled to memory 650. Memory 650 can include high-speed random access memory and or non-volatile memory, such as one or more magnetic disk storage devices, one or more optical storage devices, and or flash memory (e.g., NAND, NOR). Memory 650 can store an operating system 652, such as Darwin, RTXC, LINUX, UNIX, OS X, Windows, or an embedded operating system such as VxWorks.

Operating system 652 can include instructions for handling basic system services and for performing hardware dependent tasks. In some implementations, operating system 652 can be a kernel (e.g., UNIX kernel). In some implementations, operating system 652 can include instructions for performing voice authentication.

Memory 650 can also store communication instructions 654 to facilitate communicating with one or more additional devices, one or more computers and or one or more servers. Memory 650 can include graphical user interface instructions 656 to facilitate graphic user interface processing; sensor processing instructions 658 to facilitate sensor-related processing and functions; phone instructions 660 to facilitate phone-related processes and functions; electronic messaging instructions 662 to facilitate electronic messaging-related process and functions; web browsing instructions 664 to facilitate web browsing-related processes and functions; media processing instructions 666 to facilitate media processing-related functions and processes; GNSS/Navigation instructions 668 to facilitate GNSS and navigation-related processes and instructions; and or camera instructions 670 to facilitate camera-related processes and functions.

Memory 650 can store application (or "app") instructions and data 672, such as instructions for the apps described above in the context of FIGS. 1-6. Memory 650 can also store other software instructions 674 for various other software applications in place on device 600. The described features can be implemented in one or more computer programs that can be executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, or other unit suitable for use in a computing environment.

The described features can be implemented in one or more computer programs that can be executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, or other unit suitable for use in a computing environment.

Suitable processors for the execution of a program of instructions can include, by way of example, both general and special purpose microprocessors, and the sole processor or one of multiple processors or cores, of any kind of computer. Generally, a processor can receive instructions and data from a read-only memory or a random access memory or both. The essential elements of a computer may include a processor for executing instructions and one or more memories for storing instructions and data. Generally, a computer may also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data may include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

To provide for interaction with a user, the features may be implemented on a computer having a display device such as an LED or LCD monitor for displaying information to the user and a keyboard and a pointing device such as a mouse or a trackball by which the user may provide input to the computer.

The features may be implemented in a computer system that includes a back-end component, such as a data server, or that includes a middleware component, such as an application server or an Internet server, or that includes a front-end component, such as a client computer having a graphical user interface or an Internet browser, or any combination thereof. The components of the system may be connected by any form or medium of digital data communication such as a communication network. Examples of communication networks include, e.g., a telephone network, a LAN, a WAN, and the computers and networks forming the Internet.

The computer system may include clients and servers. A client and server may generally be remote from each other and may typically interact through a network. The relationship of client and server may arise by virtue of computer programs running on the respective computers and having a client-server relationship to each other.

One or more features or steps of the disclosed embodiments may be implemented using an API. An API may define one or more parameters that are passed between a calling application and other software code (e.g., an operating system, library routine, function) that provides a service, that provides data, or that performs an operation or a computation.

The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer will employ to access functions supporting the API.

In some implementations, an API call may report to an application the capabilities of a device running the application, such as input capability, output capability, processing capability, power capability, communications capability, etc.

While various embodiments have been described above, it should be understood that they have been presented by way of example and not limitation. It will be apparent to persons skilled in the relevant art(s) that various changes in form and detail may be made therein without departing from the spirit and scope. In fact, after reading the above description, it will be apparent to one skilled in the relevant art(s) how to implement alternative embodiments. For example, other steps may be provided, or steps may be eliminated, from the described flows, and other components may be added to, or removed from, the described systems. Accordingly, other implementations are within the scope of the following claims.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112 (f). Claims that do not expressly include the phrase "means for" or "step for" are not to be interpreted under 35 U.S.C. 112 (f).

The invention claimed is:

1. A method for determining a timing bolus delay comprising:
- administering a test bolus to a subject;
- acquiring, via a computed tomography (CT) imaging system, a plurality of non-diagnostic images of the subject at a predetermined frequency;
- determining a contrast value for each of the plurality of images;
- generating a contrast curve representing the determined contrast values versus time;
- determining a peak contrast value on the contrast curve;
- determining a prep delay based on a time corresponding to the peak contrast value; and
- administering a contrast-enhanced CT scan of the subject based on the determined prep delay.

2. The method of claim 1, wherein administering the test bolus to the subject comprises injecting a contrast agent into the subject.

3. The method of claim 1, wherein determining the prep delay based on the peak contrast value comprises an automated determination of a total elapsed time from the administering of the test bolus to the peak contrast value.

4. The method of claim 3, wherein the automated determination of the total elapsed time comprises analyzing at least one of a relative Hounsfield unit (HU) change, an absolute HU change, or a predefined percent of the peak contrast value being reached.

5. The method of claim 4 comprising:

receiving a selection from a user via a user interface; and at least one of analyzing the at least one of the relative Hounsfield unit (HU) change, the absolute HU change, or the predefined percent of the peak contrast value being reached based on the received selection.

6. The method of claim 1 comprising:

receiving a definition of a region of interest from a user via a user interface; and manipulating the contrast curve based on the definition of the region of interest.

7. The method of claim 3 comprising augmenting the total elapsed time with a predetermined modifier.

8. The method of claim 7, wherein the predetermined modifier is configured by a user via a user interface.

9. The method of claim 1, wherein acquiring the plurality of images of the subject comprises acquiring one image every second for ten seconds.

10. A method for determining a timing bolus delay comprising:

administering a test bolus to a subject;

acquiring, via a computed tomography (CT) imaging system, a plurality of non-diagnostic images of the subject at a predetermined frequency;

determining a contrast value for each of the plurality of images;

generating a contrast curve representing the determined contrast values versus time;

identifying a plateau on the contrast curve;

determining a prep delay based on a time corresponding to the identified plateau; and administering a contrast-enhanced CT scan of the subject based on the identified plateau.

11. The method of claim 10, wherein administering the test bolus to the subject comprises injecting a contrast agent into the subject.

12. The method of claim 10, wherein determining the prep delay based on the identified plateau comprises an automated determination of a total elapsed time from the administering of the test bolus to the identified plateau.

13. The method of claim 12, wherein the automated determination of the total elapsed time comprises analyzing at least one of a relative Hounsfield unit (HU) change, an absolute HU change, or a predefined percent of a peak contrast value being reached.

14. The method of claim 13 comprising:

receiving a selection from a user via a user interface; and at least one of analyzing the at least one of the relative Hounsfield unit (HU) change, the absolute HU change, or the predefined percent of the peak contrast value being reached based on the received selection.

15. The method of claim 10 comprising:

receiving a definition of a region of interest from a user via a user interface; and manipulating the contrast curve based on the definition of the region of interest.

16. The method of claim 12 comprising augmenting the total elapsed time with a predetermined modifier.

17. The method of claim 16, wherein the predetermined modifier is configured by a user via a user interface.

18. The method of claim 10, wherein the plateau occurs in a designated location after a peak contrast value.

19. The method of claim 10, wherein acquiring the plurality of images of the subject comprises acquiring one image every second for ten seconds.

20. A system for determining a timing bolus delay comprising:

a computed tomography (CT) imaging system configured to acquire a plurality of images of a subject after a test bolus has been administered to the subject; and a computing device comprising a processor and a non-transitory computer-readable storage device storing computer-executable instructions, the instructions operable to cause the processor to perform operations comprising:

receiving the plurality of non-diagnostic images of the subject from the CT imaging system acquired at a predetermined frequency;

determining a contrast value for each of the plurality of images;

generating a contrast curve representing the determined contrast values versus time;

determining a peak contrast value on the contrast curve; and determining a prep delay based on a time corresponding to the peak contrast value.

* * * * *